United States Patent
Davis et al.

(10) Patent No.: US 6,914,215 B2
(45) Date of Patent: Jul. 5, 2005

(54) REAL TIME LASER SHOCK PEENING QUALITY ASSURANCE BY NATURAL FREQUENCY ANALYSIS

(75) Inventors: Brian Michael Davis, West Chester, OH (US); Robert David McClain, Cincinnati, OH (US); Ui Won Suh, Cincinnati, OH (US); Seetha Ramaiah Mannava, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 88 days.

(21) Appl. No.: 10/608,763

(22) Filed: Jun. 27, 2003

(65) Prior Publication Data

US 2004/0262276 A1 Dec. 30, 2004

(51) Int. Cl.[7] ............................................... B23K 26/00
(52) U.S. Cl. .............................. 219/121.85; 219/121.62
(58) Field of Search ....................... 219/121.85, 121.83, 219/121.62, 121.61, 121.6

(56) References Cited

U.S. PATENT DOCUMENTS

| | | |
|---|---|---|
| 3,850,698 A | 11/1974 | Mallozzi et al. |
| 4,401,477 A | 8/1983 | Clauer et al. |
| 4,937,421 A | 6/1990 | Ortiz, Jr. et al. |
| 5,131,957 A | 7/1992 | Epstein et al. |
| 5,492,447 A | 2/1996 | Mannava et al. |
| 5,531,570 A | 7/1996 | Mannava et al. |
| 5,569,018 A | 10/1996 | Mannava et al. |
| 5,591,009 A | 1/1997 | Mannava et al. |
| 5,674,328 A | 10/1997 | Mannava et al. |
| 5,674,329 A | 10/1997 | Mannava et al. |
| 5,756,965 A | 5/1998 | Mannava |
| 5,948,293 A | 9/1999 | Somers et al. |
| 5,951,790 A | 9/1999 | Mannava et al. |
| 5,974,889 A | 11/1999 | Trantow |
| 5,987,991 A | 11/1999 | Trantow et al. |
| 5,988,982 A | 11/1999 | Clauer |
| 6,254,703 B1 | 7/2001 | Sokol et al. |
| 6,422,082 B1 | 7/2002 | Suh |
| 6,462,308 B1 * | 10/2002 | Lahrman et al. ........ 219/121.85 |
| 6,512,584 B1 | 1/2003 | O'Loughlin et al. |
| 6,629,464 B2 * | 10/2003 | Suh et al. ...................... 73/602 |
| 2003/0042234 A1 | 2/2003 | Suh et al. |
| 2003/0062349 A1 | 4/2003 | Suh et al. |

OTHER PUBLICATIONS

"Translational (Linear) Vibrations", Bruel & Kjaer Translational (Linear) Vibration.
"Laser Vibrometry", Bruel & Kjaer —Laser Vibrometry.
"Low Range Single–point Laser Doppler Vibrometer—Type 8333", Bruel & Kjaer—Low–range Single–point LDV—Type 8333.
"Scanning Laser", Bruel & Kjaer, PULSE Analyzers & Solutions, pp. 48 and 49.

* cited by examiner

*Primary Examiner*—M. Alexandra Elve
(74) *Attorney, Agent, or Firm*—William Scott Andes; Steven J. Rosen

(57) ABSTRACT

A real time method for quality control testing of a laser shock peening process of production workpieces by analysis of natural frequency shifts during the laser shock peening process. One particular embodiment includes laser shock peening surface of the production workpiece by firing a plurality of laser beam pulses on the surface and forming a plurality of corresponding plasmas, each one of the plasmas pulses having a duration in which the plasma causes a region having deep compressive residual stresses to form beneath the surface, measuring at least one natural frequency of the workpiece for each of the laser beam pulses, calculating natural frequency shifts from a baseline natural frequency for the measured natural frequencies for at least a portion of the laser beam pulses, and using the natural frequency shifts for accepting or rejecting the workpiece with respect to pass or fail criteria.

31 Claims, 6 Drawing Sheets

REAL TIME LASER SHOCK PEENING QUALITY ASSURANCE BY NATURAL FREQUENCY ANALYSIS

BACKGROUND OF THE INVENTION

1. Field of the Invention

This invention relates to quality assurance methods used for quality assurance for laser shock peening and, more particularly, for natural frequency monitoring and analysis method for quality assurance of a production laser shock peening process.

2. Discussion of the Background Art

Laser shock peening or laser shock processing, as it is also referred to, is a process for producing a region of deep compressive residual stresses imparted by laser shock peening a surface area of a workpiece. Laser shock peening typically uses multiple radiation pulses from high power pulsed lasers to produce shock waves on the surface of a workpiece similar to methods disclosed in U.S. Pat. No. 3,850,698, entitled "Altering Material Properties"; U.S. Pat. No. 4,401,477, entitled "Laser Shock Processing"; and U.S. Pat. No. 5,131,957, entitled "Material Properties". Laser shock peening, as understood in the art and as used herein, means utilizing a laser beam from a laser beam source to produce a strong localized compressive force on a portion of a surface by producing an explosive force by instantaneous ablation or vaporization of a painted or coated or uncoated surface. Laser peening has been utilized to create a compressively stressed protection layer at the outer surface of a workpiece which is known to considerably increase the resistance of the workpiece to fatigue failure as disclosed in U.S. Pat. No. 4,937,421, entitled "Laser Peening System and Method". These methods typically employ a curtain of water flowed over the workpiece or some other method to provide a confining medium to confine and redirect the process generated shock waves into the bulk of the material of a component being LSP'D to create the beneficial compressive residual stresses. Other techniques to confine and redirect the shock waves that do not use water have also been developed.

Laser shock peening is being developed for many applications in the gas turbine engine field, some of which are disclosed in the following U.S. Pat. Nos.: 5,756,965 entitled "ON THE FLY LASER SHOCK PEENING"; 5,591,009, entitled "Laser shock peened gas turbine engine fan blade edges"; 5,569,018, entitled "Technique to prevent or divert cracks"; 5,531,570, entitled "Distortion control for laser shock peened gas turbine engine compressor blade edges"; 5,492,447, entitled "Laser shock peened rotor components for turbomachinery"; 5,674,329, entitled "Adhesive tape covered laser shock peening"; and 5,674,328, entitled "Dry tape covered laser shock peening", all of which are assigned to the present Assignee. These applications, as well as others, are in need of efficient quality assurance testing during production runs using laser shock peening.

LSP is a deep treatment of the material and it is desirable to have a quality assurance test that is indicative of a volumetric LSP effect. It is also desirable to have a QA method that is compatible with a dual sided or simultaneous dual sided LSP process wherein substantially equal compressive residual stresses are imparted to both sides of a workpiece, i.e. along the leading edge of a gas turbine engine fan blade.

One laser shock peening quality assurance technique previously used is high cycle fatigue (HCF) testing of blades having leading edges which are LSP'd and notched in the LSP'd area before testing. This method is destructive of the test piece, fairly expensive and time consuming to carry out, and significantly slows production and the process of qualifying LSP'd components. An improved quality assurance method of measurement and control of LSP that is a non-destructive evaluation (NDE), inexpensive, accurate, quick, and easy to set up is highly desirable. It is also desirable to have a real time NDE quality assurance method that is relatively inexpensive and sufficiently economical to be used on each workpiece instead of a sampling of workpieces. LSP is a process that, as any production technique, involves machinery and is time consuming and expensive. It is desirable to have a real time NDE method so that process deviations can be discovered during a production run. Therefore, any real time techniques that can reduce the amount or complexity of production machinery and/or production time are highly desirable.

Interferometric profilometry method and apparatus to obtain volumetric data of a single laser shock peened test dimple created with a single firing of a laser used in the laser shock peening process is disclosed in U.S. Pat. No. 5,948,293, entitled "Laser shock peening quality assurance by volumetric analysis of laser shock peened dimple". Other QA methods are disclosed in U.S. Pat. No. 5,987,991, entitled "Determination of Rayleigh wave critical angle"; U.S. Pat. No. 5,974,889, entitled "Ultrasonic multi-transducer rotatable scanning apparatus and method of use thereof"; and U.S. Pat. No. 5,951,790, entitled "Method of monitoring and controlling laser shock peening using an in plane deflection test coupon". U.S. Pat. No. 6,254,703, entitled "Quality Control Plasma Monitor for Laser Shock Processing" discloses a method and apparatus for quality control of laser shock processing by measuring emissions and characteristics of a workpiece when subjected to a pulse of coherent energy from a laser. U.S. patent application Ser. No. 09/969,744, filed Oct. 3, 2001, and entitled "LASER SHOCK PEENING QUALITY ASSURANCE BY ACOUSTIC ANALYSIS" discloses a method for quality control of laser shock processing by measuring an acoustic signal for each laser beam pulse, calculating an acoustic energy parameter value for each of the acoustic signals, and calculating a statistical function value of the workpiece based on the acoustic energy parameter values. These empirically measured emissions and characteristics of the workpiece are correlated to theoretical shock pressure, residual stress profile, or fatigue life of the workpiece. These methods typically use a radiometer or acoustic detection device for measuring these characteristics.

SUMMARY OF THE INVENTION

A real time method for quality control testing of a laser shock peening process of production workpieces uses analysis of natural frequency shifts during the laser shock peening process. One particular embodiment of the method includes (a) laser shock peening surface of the production workpiece by firing a plurality of laser beam pulses from a laser shock peening system on the surface of the production workpiece and forming a plurality of corresponding plasmas, each one of the plasmas for each one of the pulses having a duration in which the plasma causes a region to form beneath the surface, the region having deep compressive residual stresses imparted by the laser shock peening process, (b) measuring at least one natural frequency for each of the laser beam pulses during a period of time during the duration of each corresponding one of the plasmas, (c) calculating natural frequency shifts from the measured natural frequencies for at least a portion of the laser beam pulses, and (d) using the natural frequency shifts for accepting or rejecting the workpiece with respect to pass or fail criteria for quality assurance of the laser shock peening process.

The pass or fail criteria may be based on a pre-determined correlation of measured test piece natural frequency shifts and high cycle fatigue failure from high cycle fatigue tests of test pieces that were laser shock peened in the same or similar laser shock peening apparatus. The test pieces may each include a failure precipitating flaw within a laser shock peened area of the test piece that was laser shock peened in the same or similar laser shock peening apparatus.

The method may include calculating a statistical function value of the workpiece based on the natural frequency shifts and comparing the statistical function value to a pass or fail criteria for quality assurance of the laser shock peening process for accepting or rejecting the workpiece. The statistical function values may be calculated using a statistical function. Exemplary statistical functions include an average of at least a portion of the natural frequency shifts, a standard deviation of at least a portion of the natural frequency shifts, and a trend of at least a portion of the natural frequency shifts.

The measuring may be performed using a contact vibration sensor, such as an accelerometer, connected to the workpiece. The measuring may be performed using a microphone or a non-contact laser gage spaced away from the workpiece. The natural frequency shifts may be differences between the measured natural frequencies for at least a portion of the laser beam pulses and a baseline natural frequency. The baseline natural frequency may be one of the measured natural frequencies such as a first one of the measured natural frequencies. The baseline natural frequency may be a measured natural frequency of a non-laser shock peened test piece and the non-laser shock peened test piece may be the workpiece before it is laser shock peened.

The real time natural frequency laser shock peening quality assurance method provides efficient, reliable, and repeatable quality assurance testing during laser shock peening production runs. The quality assurance method of measurement and control of LSP that is a non-destructive evaluation (NDE), inexpensive, accurate, quick, and easy to set up. This method provides a real time NDE quality assurance method that is relatively inexpensive and sufficiently economical to be used on each workpiece instead of a sampling of workpieces. This real time NDE method allows deviations to be discovered during a production run resulting in lower scrap rates and less wasted production time.

BRIEF DESCRIPTION OF THE DRAWINGS

The foregoing aspects and other features of the invention are explained in the following description, taken in connection with the accompanying drawings where.

DETAILED DESCRIPTION

Figure 1:
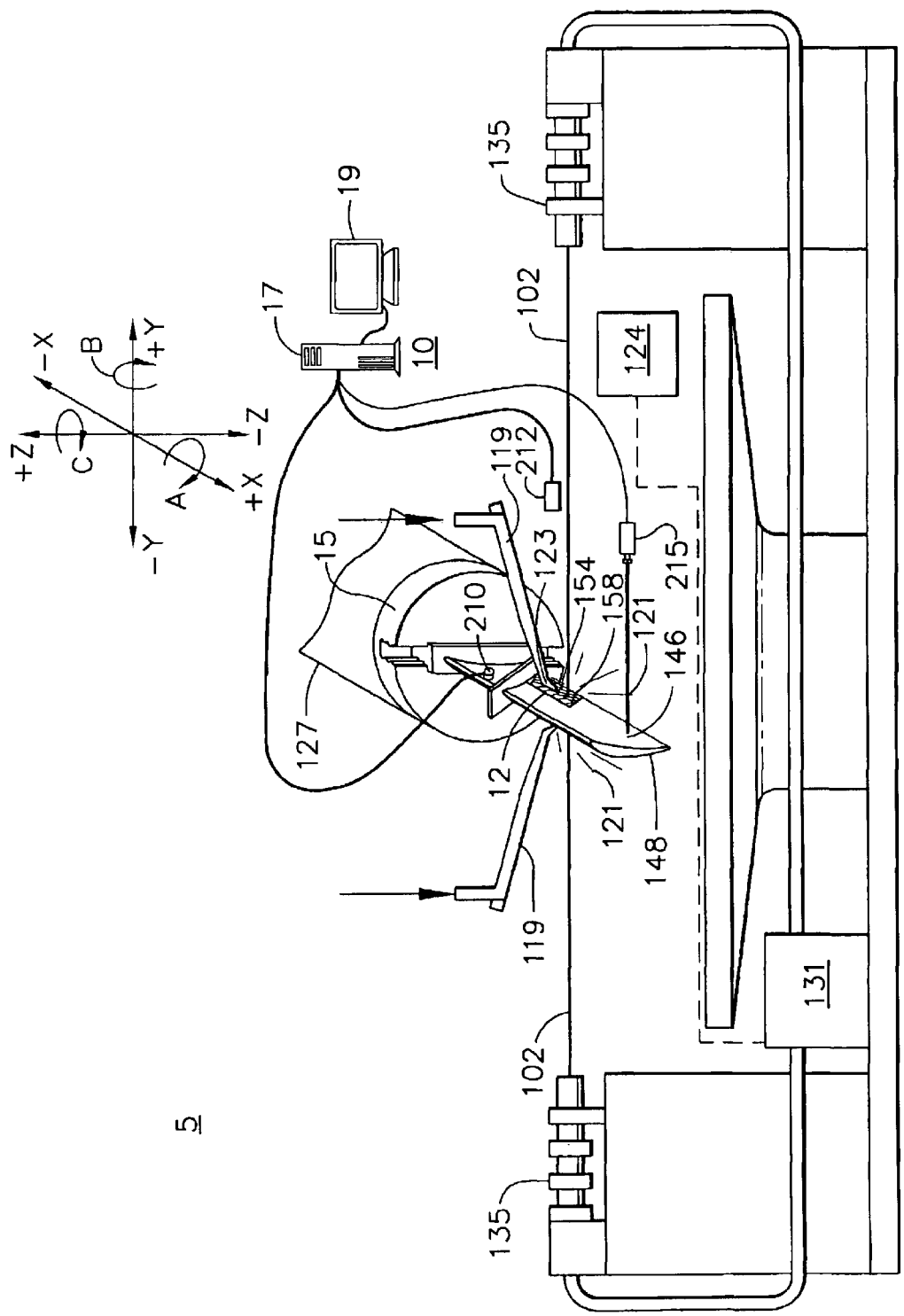
FIG. 1 is a diagrammatic illustration of a laser shock peening system with a natural frequency monitoring system for quality assurance of a production laser shock peening process in an exemplary embodiment of a method for quality assurance by natural frequency monitoring of a production laser shock peening process.
Figure 2:
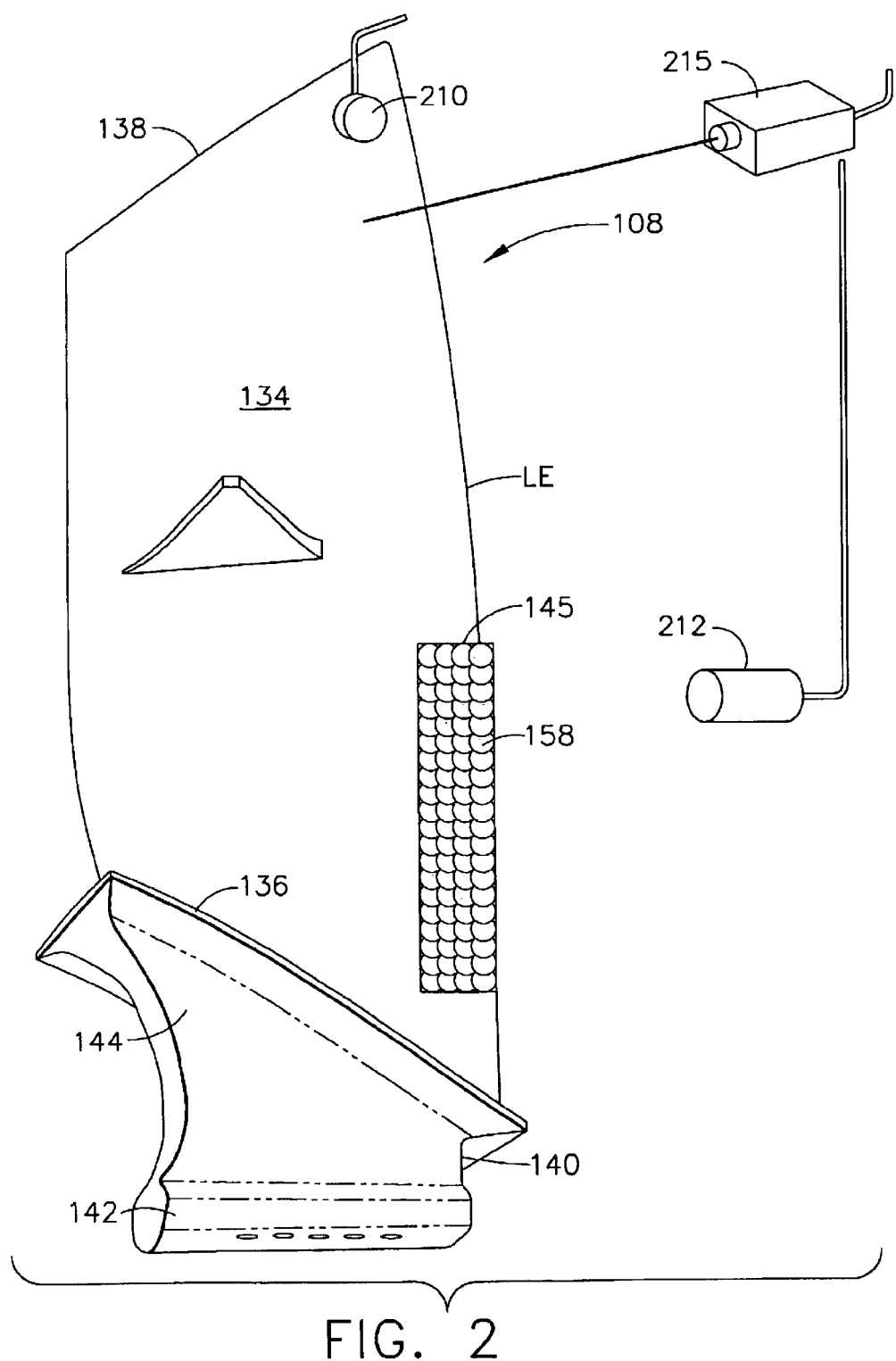
FIG. 2 is a perspective view illustration of a production fan blade exemplifying a laser shock peened production workpiece and natural frequency measuring devices used in the exemplary embodiment of the method.

Quality assurance is typically a go or no go, pass or fail, accept or reject type of analysis. A system for measuring natural frequencies 202, illustrated in FIG. 3, during laser shock peening, calculating natural frequency shifts 204, and using the shifts for quality assurance of the laser shock peening process on a production workpiece such as an exemplary aircraft turbofan gas turbine engine production fan blade 108 is illustrated in FIGS. 1, 2, and 4. Illustrated in FIG. 1 is a diagrammatic representation of a laser shock peening system 5 having a natural frequency monitoring system 10. The laser shock peening system 5 has a conventional laser beam generator 131 with an oscillator, a pre-amplifier, a beam splitter which feeds the pre-amplified laser beam into two beam optical transmission circuits each having a first and second amplifier, and optics 135 which include optical elements that transmit and focus the laser beams 102 on the coated surfaces of the production fan blade 108 or workpiece.

The natural frequency monitoring system 10 is used to perform a quality assurance method for quality control of a laser shock peening process. The quality assurance of a laser shock peening process on a production workpiece is exemplified for the exemplary aircraft turbofan gas turbine engine production fan blade 108 or other object made of a metallic material as disclosed in U.S. Pat. Nos. 5,492,447, 5,674,329, 5,674,328, and 5,591,009. The quality assurance method are NDE tests designed to be performed during laser shock peening of each workpiece.

Figure 3:
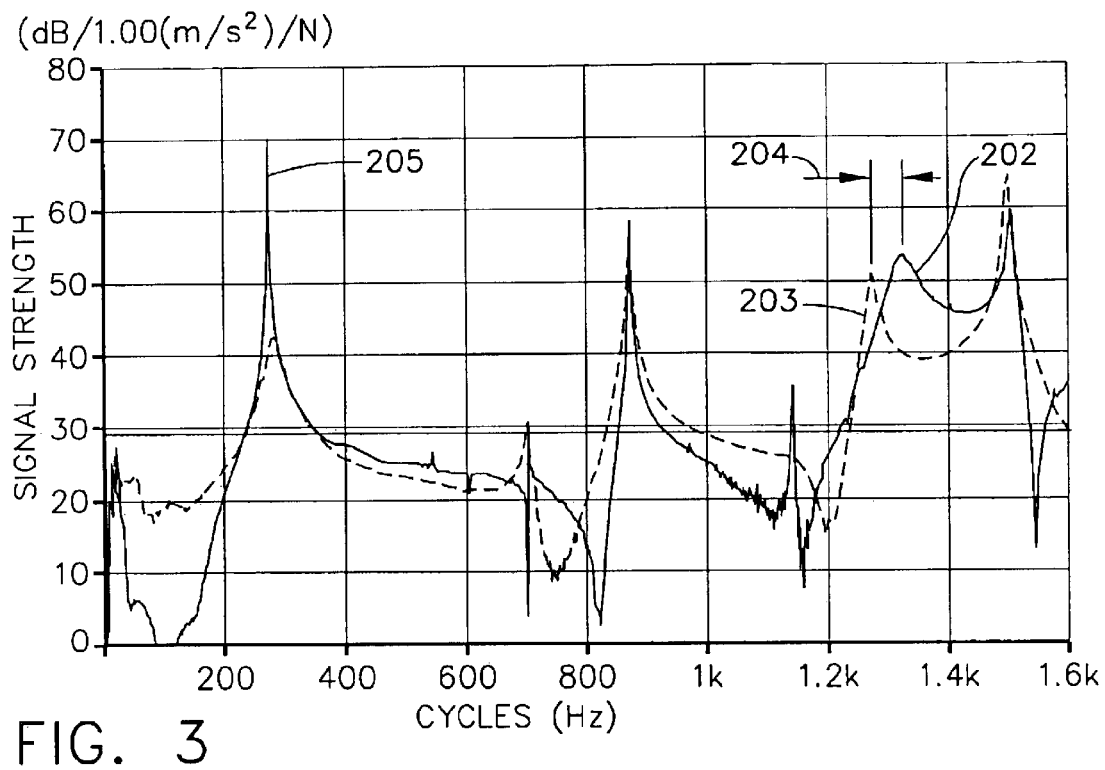
FIG. 3 is an illustration of a screen depicting a natural frequency shift during the laser shock peening process.
Figure 4:
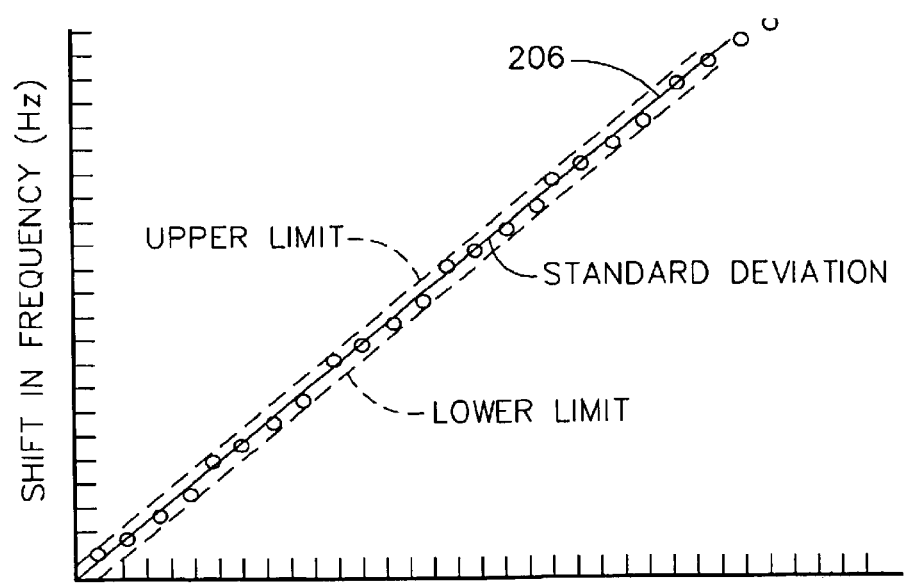
FIG. 4 is an illustration of a screen depicting a plot of natural frequencies shifts for a plurality of laser beam hits during the laser shock peening process producing laser shock peening spots.

Several natural frequencies may be excited for different modes as exemplified by the peaks 205 in the vibration plot illustrated in FIG. 3. One or more of the natural frequencies of these peaks shift with each laser beam hit during laser shock peening. Natural frequency shifts 204 of one mode (more modes can be used) is chosen to be analyzed. For the example in FIG. 3 the third mode has been chosen and natural frequency shifts 204 of the third mode are monitored and analyzed. During production runs, a plurality of if not all or almost all natural frequency shifts 204 are compared to pre-determined pass/fail criteria such as a high cycle fatigue correlation for passing or failing the workpieces. As each laser beam shot is made, the natural frequency 202 will change as will the natural frequency shift 204 from a baseline as illustrated in FIG. 4.

Referring to FIG. 1, the laser shock peening system 5 for laser shock peening the production fan blade 108 is illustrated with the fan blade mounted in a fixture 15 which is attached to a five-axis computer numerically controlled (CNC) manipulator 127. Five axes of motion illustrated in the exemplary embodiment are conventional translational axes X, Y, and Z, and conventional rotational axes A, B and C which are well known in CNC machining. The manipulator 127 moves and positions the production fan blades 108 and test fan blades 109 to effect laser shock peening on the fly. Laser shock peening may be done in a number of various ways using an ablative coating such as paint or tape as an ablative medium (see U.S. Pat. No. 5,674,329, entitled "Adhesive Tape Covered Laser Shock Peening"). Laser shock peening may also be done without a coating. The same laser shock peening system 5 is used in the laser shock peening process of the leading edge section 150 of the production fan blade 108 and the test fan blades 109 (representing the test pieces and workpieces).

Figure 5:
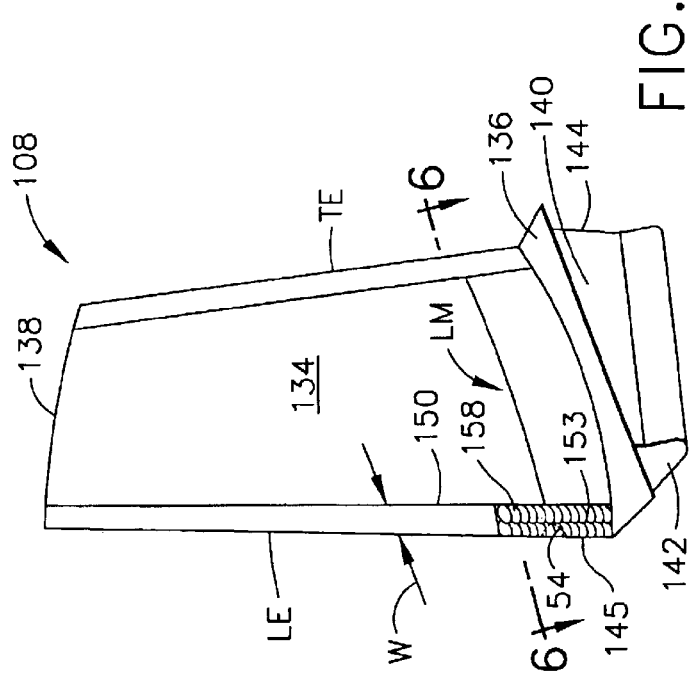
FIG. 5 is a perspective view illustration of a laser shock peened blade exemplifying a workpiece in the exemplary embodiment of the method.
Figure 6:
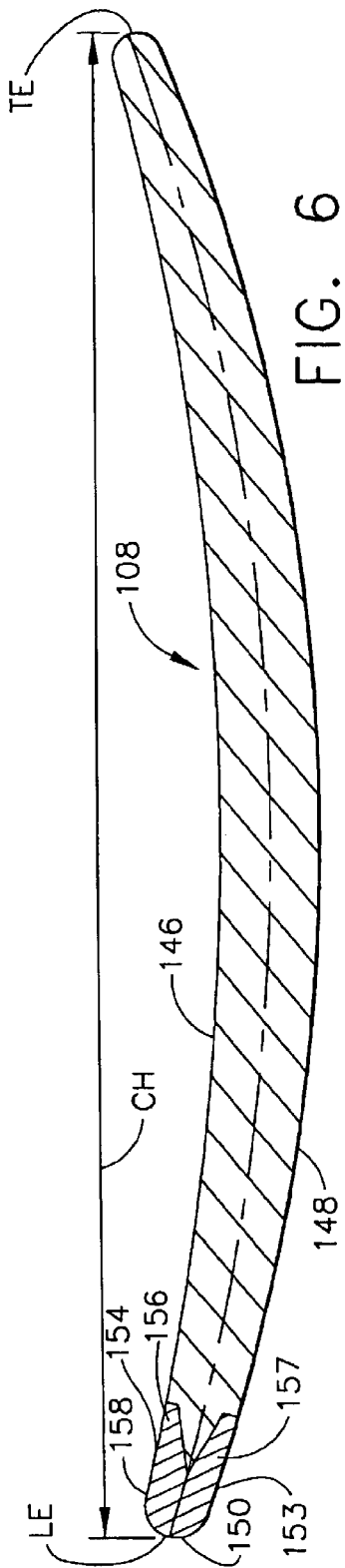
FIG. 6 is a cross-sectional view illustration of the fan blade through 6—6 in FIG. 5.

Referring to FIGS. 5 and 6, the production fan blade 108 includes an airfoil 134 extending radially outward from a blade platform 136 to a blade tip 138 and a root section 140 extending radially inward from the platform 136. The root section 140 has a blade root 142 connected to the platform 136 by a blade shank 144. The airfoil 134 extends in a chordwise direction between a leading edge LE and a trailing edge TE of the airfoil. The fan blade 12 has a leading edge section 150 that extends along the leading edge LE of the airfoil 134 from the production fan blade platform 136 to the production fan blade tip 138. The airfoil 134 has a pressure side 146 and a suction side 148 extending between the leading edge and trailing edges LE and TE of the airfoil. A chord CH of the airfoil 134 extends between the leading LE and trailing edge TE at each cross-section of the production fan blade as illustrated in FIG. 6. The leading edge section 150 includes a pre-determined first width W such that the leading edge section 150 encompasses an area where nicks 54 and tears that may occur along the leading edge of the airfoil 134 during engine operation. The airfoil 134 subject to a significant tensile stress field due to centrifugal forces generated by the production fan blade 108 rotating during engine operation. The airfoil 134 is also subject to vibrations generated during engine operation and the nicks 54 and tears operate as high cycle fatigue stress risers producing additional stress concentrations around them.

To counter fatigue failure of portions of the production fan blade along possible crack lines that can develop and emanate from the nicks and tears, a laser shock peened patch 145 is placed along a portion of the leading edge LE where incipient nicks and tears may cause a failure of the production fan blade due to high cycle fatigue. Laser shock peening produces laser shock peening spots 158 within the laser shock peened patch 145. In the exemplary embodiment of the quality assurance method illustrated herein, the pressure side 146 and the suction side 148 are simultaneously laser shock peened to form pressure side and suction side laser shock peened surfaces 154 and 153 and corresponding pressure side and suction side pre-stressed regions 156 and 157, respectively, having deep compressive residual stresses imparted by laser shock peening (LSP) extending into the airfoil 134 from the laser shock peened surfaces as seen in FIG. 6. The pre-stressed regions are illustrated along only a portion of the leading edge section 150 but may extend along the entire leading edge LE or longer portion thereof if so desired. The pre-determined criteria of the exemplary embodiment is based on a correlation of one or more functions of acoustic intensity data versus high cycle fatigue data of test versions of the workpieces that are exemplified by laser shock peened and notched test fan blades 109 having a notch 152 illustrated in FIG. 7. In the exemplary embodiments of the method, the production and test fan blades 108 and 109, respectively, are laser shock peened the same way during production runs and HCF testing runs for the correlation.

Figure 7:
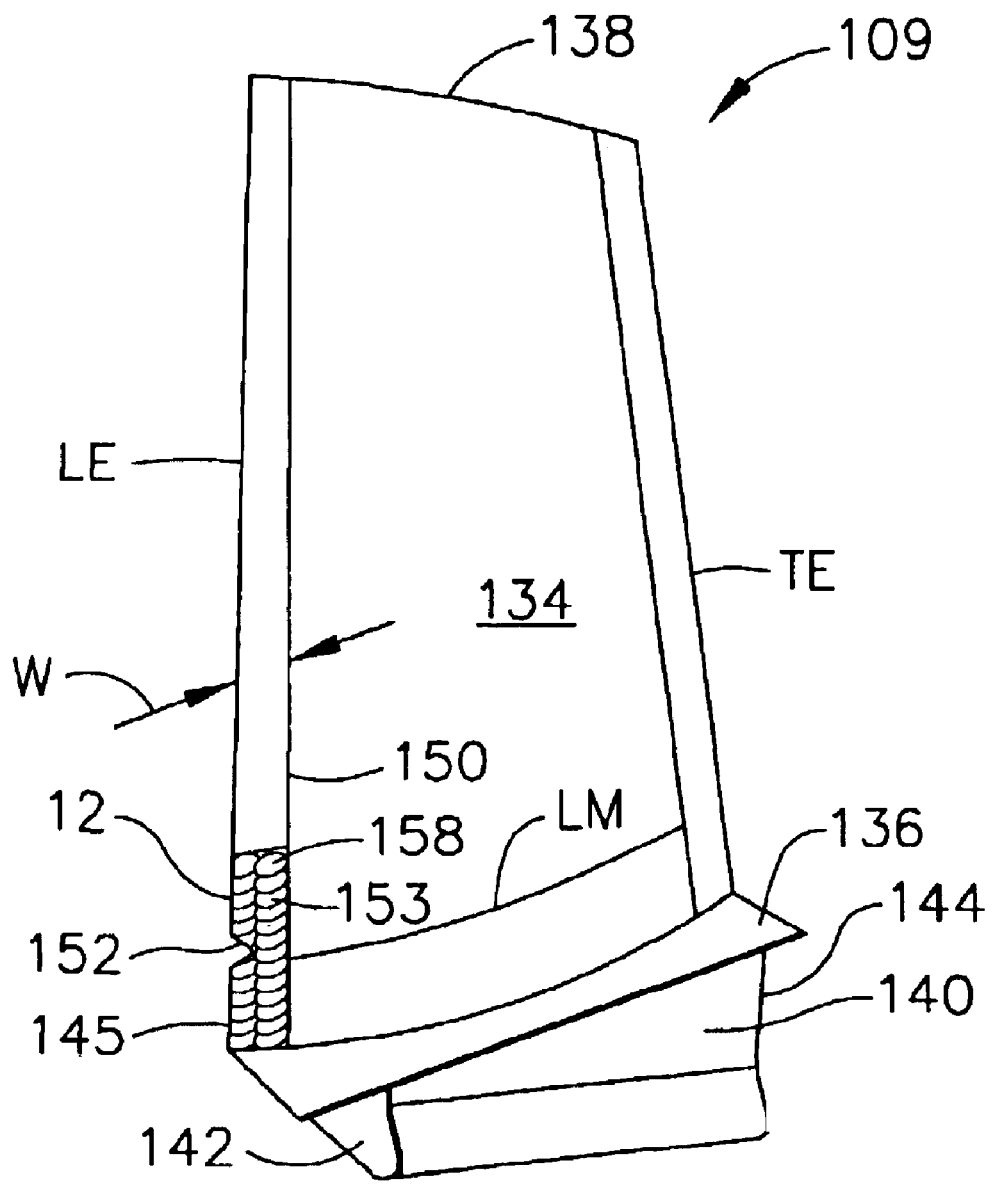
FIG. 7 is a perspective view illustration of a laser shock peened blade with a notch exemplifying a test piece corresponding to the workpiece illustrated in FIG. 5 which is used to determine a correlation between high cycle fatigue failure and natural frequency shifts due to laser shock peening.

The high cycle fatigue (HCF) correlation of the test fan blades 109 in the exemplary embodiments of the method is based on fatigue testing of the laser shock peened and notched test fan blades 109 as illustrated in FIG. 7. The test fan blades 109 are full scale and notched to precipitate a failure. The test pieces or test fan blades 109 are made the same way as the actual production fan blades 108 with a notch 152 added after the test fan blade 109 is laser shock peened to form the patch 145.

The laser shock peened test fan blades 109 are monitored for natural frequency shifts and analyzed in the same manner as the production blades 108. The HCF testing may be used to establish pass/fail criteria for use during production runs to be compared to the results of the analysis from the natural frequency shift monitoring and analysis. The laser shock peened test fan blades 109 are vibrated at a chosen mode (or modes) frequency until it fails. A number of test fan blades 109 or just one test fan blade 109 may be notched and subjected to high cycle fatigue tests to establish the correlation. For high cycle fatigue, each laser shock peened test fan blade 109 has a notch 152, representing a failure precipitating flaw, placed in the laser shock peened patch 145. The notch 152 is placed at a pre-determined position of the pre-stressed regions 157 and 156 after the production fan blade is laser shock peened. The notch 152 may be centered about a pre-determined mode line such as a first mode line LM. If tested blade meets standards or test criteria on length of time and amplitude of the forcing function that is exiting the production fan blade, then it is acceptable. These results can then be used during production runs to continuously monitor quality of the laser shock peening process. The process may be stopped and the laser shock peening system may be based on the natural frequency shift analysis of the data fixed and/or the production part may be scrapped or pulled out of the line for further analysis later.

The area to be laser shock peened and form the laser shock peened patch 145, the pressure and suction side laser shock peened surfaces 154 and 153 are covered with an ablative coating such as paint or adhesive tape to form a coated surface as disclosed in U.S. Pat. Nos. 5,674,329 and 5,674,328. The coating provides an ablative medium over which is a clear containment medium which may be a clear fluid curtain such as a curtain of flowing water 121.

The laser beam shock induced deep compressive residual stresses may be produced by repetitively firing two high power laser beams 102, each of which is defocused plus or minus a few mils with respect to the coated pressure side and suction side laser shock peened surfaces 154 and 153 of the pressure side 146 and the suction side 148 of the production fan blade 108. Each of the laser beams is fired through the curtain of flowing water 121 supplied by a conventional water nozzle 123 at the end of a conventional water supply tube 119. The curtain of flowing water 121 is flowed over the coated surfaces. The coating is ablated generating plasma which results in shock waves on the surface of the material. Other ablative materials may be used to coat the surface as suitable alternatives to paint. These coating materials include metallic foil or adhesive plastic tape as disclosed in U.S. Pat. Nos. 5,674,329 and 5,674,328. These shock waves are re-directed towards the coated surfaces by the curtain of flowing water 121 to generate travelling shock waves (pressure waves) in the material below the coated surfaces. The amplitude and quantity of these shock waves determine the depth and intensity of compressive stresses. The ablative coating is used to protect the target surface and also to generate plasma. The laser beam shock induced deep compressive residual stresses in the compressive pre-stressed regions are generally about 50–150 KPSI (Kilo Pounds per Square Inch) extending from the laser shock peened surfaces to a depth of about 20–50 mils into the pre-stressed regions. Low powered laser beams of 3–10 joules or even perhaps 1–10 joules may be used with circularly shaped laser shock peening spots 158 having a diameter of about 8 mm. Other shapes for the laser shock peening spots 158 may be used. By way of example oblique circular cross-section laser beams produce elliptically shaped laser shock peening spots 158 which may also be used in the present quality assurance method.

The production fan blade 108 is continuously moved while the stationary high power laser beams 102 are continuously firing through the curtain of flowing water 121 on the coated (or uncoated) pressure and suction side laser shock peened surfaces 154 and 153 and forming spaced apart circular laser shock peened spots 158. The production fan blades 108 are laser shock peened the same way during production runs and HCF testing runs for the correlation. A controller 124 is be used to modulate and control the laser shock peening system 5 to fire the laser beams 102 on the coated surfaces in a controlled manner. Ablated coating material is washed out by the curtain of flowing water 121.

Referring to FIGS. 2, 3 and 4, the natural frequency monitoring system 10 is used to perform a real time NDE method for quality control testing of a laser shock peening process of production fan blades 108 or workpieces by analysis of natural frequency shifts 204 due to at least a plurality of firings of the laser beams during the laser shock peening process. One particular embodiment of the method includes the following steps: Step (a) laser shock peening surface 153 of the production workpiece by firing a plurality of laser beam 102 pulses from a laser shock peening system 5 on the surface of the production workpiece and forming a plurality of corresponding plasmas. Each one of the plasmas for each one of the pulses has a duration in which the plasma causes a region 157 to form beneath the surface. The region has deep compressive residual stresses imparted by the laser shock peening process. Step (b) includes measuring at least one natural frequency 202 for each of the laser beam 102 pulses during a period of time during the duration of each corresponding one of the plasmas. Step (c) includes calculating natural frequency shifts 204 from the measured natural frequencies 202 for at least a portion of the laser beam 102 pulses. Step (d) includes using the natural frequency shifts 204 for accepting or rejecting the workpiece with respect to pass or fail criteria for quality assurance of the laser shock peening process.

The pass or fail criteria may be based on a pre-determined correlation of measured test piece natural frequencies 202 and high cycle fatigue failure from high cycle fatigue tests of test pieces 109 that were laser shock peened in the same or similar laser shock peening apparatus. The test pieces 109 may each include a failure precipitating flaw within a laser shock peened area of the test piece that was laser shock peened in the same or similar laser shock peening apparatus.

The measuring of natural frequencies may be performed using a contact vibration sensor 210, such as an accelerometer, connected to fan blade 108 or another workpiece as illustrated in FIGS. 1 and 2. The contact vibration sensor 210 is illustrated as being mounted on the production fan blade 108 or workpiece but it may be mounted on the fixture or elsewhere that is connected to the workpiece. The measuring may also be performed using a microphone 212 or a non-contact laser gage 215 spaced away from the workpiece or blade 108. Non-contact laser gages 215 are well known and such laser vibrometers are available from Bruel & Kjaer 2815-A Colonnades Court, Norcross, Ga. 30071-1588. Natural frequency signal data from the vibration sensors are transmitted to a computer 17 for analysis of the data. A monitor 19 of the computer 17 can be used to display the frequency data as illustrated in FIG. 3 and results of the analysis of the data to show the natural frequencies and the shifts in natural frequencies as compared to the pass or fail criteria for quality assurance of the laser shock peening process for accepting or rejecting the workpiece such as upper and lower limits as illustrated in FIG. 4.

The natural frequency shifts 204 may be differences between the measured natural frequencies 202 for at least a portion of the laser beam 102 pulses and a baseline natural frequency 203. The baseline natural frequency 203 may be one of the measured natural frequencies 202 such as a first one of the measured natural frequencies 202. The baseline natural frequency 203 may be a measured natural frequency of a non-laser shock peened test piece and the non-laser shock peened test piece may be the workpiece represented by the production fan blade 108 before it is laser shock peened.

The method may include calculating a statistical function value 206 of the workpiece based on the natural frequency shifts 204 and comparing the statistical function value to a pass or fail criteria for quality assurance of the laser shock peening process for accepting or rejecting the workpiece. The statistical function values 206 may be calculated using a statistical function. Exemplary statistical functions include an average of at least a portion of the natural frequency shifts 204, a standard deviation of at least a portion of the natural frequency shifts 204, and a trend of at least a portion of the natural frequency shifts 204.

Figure 8:
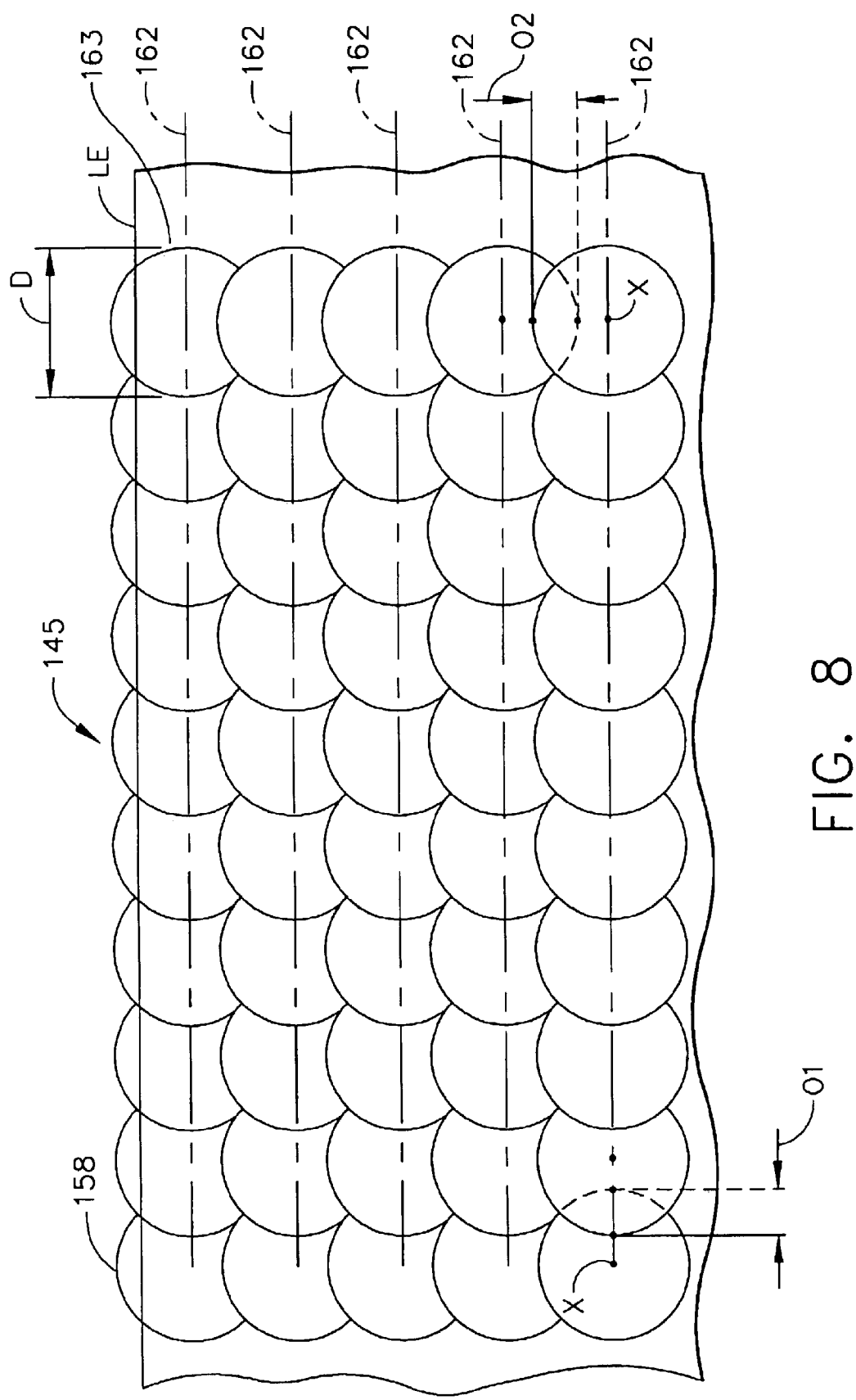
FIG. 8 is a diagrammatic side view illustration of a pattern of circular laser shock peened spots formed in first and second layers of an exemplary laser shock peening process.

The present invention provides efficient, reliable, and repeatable quality assurance testing during production runs using laser shock peening. The real time NDE method of the present invention allows deviations to be discovered during a production run resulting in lower scrap rates and less wasted production time. The signals used are from a plurality of laser beam 102 pulses. The exemplary embodiment uses data from all the pulses illustrated as laser shock peening spots 158 on the laser shock peened surface 153 in FIG. 8. The surface is typically laser shock peened with more than one sequence of coatings of the surface and then firings of the laser beams on the surface such that adjacent laser shock peened spots are hit in different sequences or passes of the laser beams forming layers of overlapping laser shock peening spots 158. The pattern of sequences entirely covers the laser shock peened surface 153. The circular laser shocked peened spots 158 have a diameter D in a row 163 of overlapping laser shock peened spots. A first overlap is between adjacent circular laser shock peened spots 158 in a given row and is generally defined by a first offset O1 between centers X of the adjacent laser shock peened spots 158 and can vary from about 30%–50% or more of the diameter D. A second overlap is between adjacent laser shock peened spots 158 in adjacent rows and is generally defined by a second offset O2 between adjacent row centerlines 162 and can vary from about 30%–50% of the diameter D depending on applications and the strength or fluency of the laser beam.

The blades may be continuously moved while continuously firing the laser beam on the taped surface. Adjacent laser shock peened spots may be hit in different sequences. However, the laser beam may be moved instead just so long as relative movement between the beam and the surface is effected.

While there have been described herein what are considered to be preferred and exemplary embodiments of the present invention, other modifications of the invention shall be apparent to those skilled in the art from the teachings herein and, it is therefore, desired to be secured in the appended claims all such modifications as fall within the true spirit and scope of the invention. Accordingly, what is desired to be secured by Letters Patent of the United States is the invention as defined and differentiated in the following claims.

We claim:

1. A method for quality control testing of a laser shock peening process of production workpieces, the method comprising the following steps:
   (a) laser shock peening surface of the production workpiece by firing a plurality of laser beam pulses from a laser shock peening system on the surface of the production workpiece and forming a plurality of corresponding plasmas, each one of the plasmas for each one of the pulses having a duration in which the plasma causes a region to form beneath the surface, the region having deep compressive residual stresses imparted by the laser shock peening process,
   (b) measuring at least one natural frequency for each of the laser beam pulses during a period of time during the duration of each corresponding one of the plasmas,
   (c) calculating natural frequency shifts from a baseline natural frequency for the measured natural frequencies for at least a portion of the laser beam pulses, and
   (d) using the natural frequency shifts for accepting or rejecting the workpiece with respect to pass or fail criteria for quality assurance of the laser shock peening process.

2. A method as claimed in claim 1 wherein the pass or fail criteria is based on a pre-determined natural frequency shift correlation based on measured test piece natural frequencies and high cycle fatigue failure from high cycle fatigue tests of test pieces that were laser shock peened in the same or similar laser shock peening apparatus.

3. A method as claimed in claim 2 wherein each of the test pieces included a failure precipitating flaw within a laser shock peened area of the test piece that was laser shock peened in the same or similar laser shock peening apparatus.

4. A method as claimed in claim 1 wherein the measuring is performed using a contact vibration sensor connected to the workpiece.

5. A method as claimed in claim 4 wherein the pass or fail criteria is based on a pre-determined natural frequency shift correlation based on measured test piece natural frequencies and high cycle fatigue failure from high cycle fatigue tests of test pieces that were laser shock peened in the same or similar laser shock peening apparatus.

6. A method as claimed in claim 5 wherein each of the test pieces included a failure precipitating flaw within a laser shock peened area of the test piece that was laser shock peened in the same or similar laser shock peening apparatus.

7. A method as claimed in claim 4 wherein the vibration sensor is mounted on the workpiece.

8. A method as claimed in claim 7 wherein the pass or fail criteria is based on a pre-determined natural frequency shift correlation based on measured test piece natural frequencies and high cycle fatigue failure from high cycle fatigue tests of test pieces that were laser shock peened in the same or similar laser shock peening apparatus.

9. A method as claimed in claim 7 wherein each of the test pieces included a failure precipitating flaw within a laser shock peened area of the test piece that was laser shock peened in the same or similar laser shock peening apparatus.

10. A method as claimed in claim 1 wherein the measuring is performed using a microphone spaced away from the workpiece.

11. A method as claimed in claim 10 wherein the pass or fail criteria is based on a pre-determined natural frequency shift correlation based on measured test piece natural frequencies and high cycle fatigue failure from high cycle fatigue tests of test pieces that were laser shock peened in the same or similar laser shock peening apparatus.

12. A method as claimed in claim 11 wherein each of the test pieces included a failure precipitating flaw within a laser shock peened area of the test piece that was laser shock peened in the same or similar laser shock peening apparatus.

13. A method as claimed in claim 1 wherein the measuring is performed using a non-contact laser gage.

14. A method as claimed in claim 13 wherein the pass or fail criteria is based on a pre-determined natural frequency shift correlation based on measured test piece natural frequencies and high cycle fatigue failure from high cycle fatigue tests of test pieces that were laser shock peened in the same or similar laser shock peening apparatus.

15. A method as claimed in claim 14 wherein each of the test pieces included a failure precipitating flaw within a laser shock peened area of the test piece that was laser shock peened in the same or similar laser shock peening apparatus.

16. A method as claimed in claim 1 wherein the natural frequency shifts are differences between the measured natural frequencies for at least a portion of the laser beam pulses and the baseline natural frequency.

17. A method as claimed in claim 16 wherein the baseline natural frequency is one of the measured natural frequencies.

18. A method as claimed in claim 16 wherein the baseline natural frequency is a first one of the measured natural frequencies.

19. A method as claimed in claim 16 wherein the baseline natural frequency is a measured natural frequency of a non-laser shock peened test piece.

20. A method as claimed in claim 19 wherein the non-laser shock peened test piece is the workpiece before it is laser shock peened.

21. A method as claimed in claim 16 wherein each of the test pieces included a failure precipitating flaw within a laser shock peened area of the test piece that was laser shock peened in the same or similar laser shock peening apparatus.

22. A method for quality control testing of a laser shock peening process of production workpieces, the method comprising the following steps:
   (a) laser shock peening surface of the production workpiece by firing a plurality of laser beam pulses from a laser shock peening system on the surface of the production workpiece and forming a plurality of corresponding plasmas, each one of the plasmas for each one of the pulses having a duration in which the plasma causes a region to form beneath the surface, the region having deep compressive residual stresses imparted by the laser shock peening process,
   (b) measuring at least one natural frequency for each of the laser beam pulses during a period of time during the duration of each corresponding one of the plasmas,
   (c) calculating natural frequency shifts from a baseline natural frequency for the measured natural frequencies for the measured natural frequencies for at least a portion of the laser beam pulses,
   (d) calculating a statistical function value of the workpiece based on the natural frequency shifts, and
   (e) comparing the statistical function value to a pass or fail criteria for quality assurance of the laser shock peening process for accepting or rejecting the workpiece.

23. A method as claimed in claim 22 wherein the statistical function values are calculated using a statistical function chosen from of a group of statistical functions consisting of an average of at least a portion of the natural frequency shifts, a standard deviation of at least a portion of the natural frequency shifts, and a trend of at least a portion of the natural frequency shifts.

24. A method as claimed in claim 23 wherein the natural frequency shifts are differences between the measured natural frequencies for at least a portion of the laser beam pulses and the baseline natural frequency.

25. A method as claimed in claim 24 wherein the baseline natural frequency is one of the measured natural frequencies.

26. A method as claimed in claim 24 wherein the baseline natural frequency is a first one of the measured natural frequencies.

27. A method as claimed in claim 24 wherein the baseline natural frequency is a measured natural frequency of a non-laser shock peened workpiece.

28. A method as claimed in claim 22 wherein the measuring is performed using a contact vibration sensor connected to the workpiece.

29. A method as claimed in claim 28 wherein the vibration sensor is mounted on the workpiece.

30. A method as claimed in claim 22 wherein the measuring is performed using a microphone spaced away from the workpiece.

31. A method as claimed in claim 22 wherein the measuring is performed using a non-contact laser gage spaced away from the workpiece.

* * * * *